(12) United States Patent  
Brannan (10) Patent No.: US 12,414,818 B2
(45) Date of Patent: Sep. 16, 2025

(54) INTERNALLY COOLED CERAMIC ELEMENT FOR A MICROWAVE ABLATION RADIATOR AND METHOD

(71) Applicant: Covidien LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 935 days.

(21) Appl. No.: 17/310,036

(22) PCT Filed: Feb. 4, 2020

(86) PCT No.: PCT/US2020/016474
§ 371 (c)(1),
(2) Date: Jul. 13, 2021

(87) PCT Pub. No.: WO2020/163253
PCT Pub. Date: Aug. 13, 2020

(65) Prior Publication Data
US 2022/0061917 A1     Mar. 3, 2022

Related U.S. Application Data

(60) Provisional application No. 62/801,691, filed on Feb. 6, 2019.

(51) Int. Cl.
*A61B 18/18* (2006.01)
*A61B 18/00* (2006.01)

(52) U.S. Cl.
CPC .............................. *A61B 18/1815* (2013.01); *A61B 2018/00023* (2013.01); *A61B 2018/00166* (2013.01);
(Continued)

(58) Field of Classification Search
CPC .................................................. A61B 18/1815
See application file for complete search history.

(56) References Cited

U.S. PATENT DOCUMENTS

2007/0073285 A1* 3/2007 Peterson ............ A61B 18/1477
606/41
2009/0005766 A1    1/2009 Brannan
(Continued)

FOREIGN PATENT DOCUMENTS

AU      2017245452 A1    11/2017
CN       102711643 A     10/2012
(Continued)

OTHER PUBLICATIONS

International Search Report and Written Opinion of the International Searching Authority issued in corresponding application, PCT/US2020/016474 mailed May 28, 2020 (17 pages).
(Continued)

*Primary Examiner* — Ronald Hupczey, Jr.
(74) *Attorney, Agent, or Firm* — Carter, DeLuca & Farrell LLP (57) ABSTRACT

A microwave antenna for ablating tissue in a patient includes a radiator configured to radiate microwave radiation. A cable is coupled to the radiator and includes a fluid inflow line and a fluid outflow line. The microwave antenna also includes a ceramic element coaxially disposed around the radiator. The ceramic element includes at least one internal channel configured to transport thermal energy away from the ceramic element.

18 Claims, 5 Drawing Sheets

(52) U.S. Cl.
  CPC ............... *A61B 2018/00577* (2013.01); *A61B 2018/1892* (2013.01)

(56) References Cited

U.S. PATENT DOCUMENTS

| | | | |
|---|---|---|---|
| 2010/0053015 A1 | 3/2010 | Willyard | |
| 2011/0066144 A1* | 3/2011 | Bonn | ................. A61B 18/1815 29/600 |
| 2011/0077635 A1* | 3/2011 | Bonn | ...................... H01Q 9/16 343/906 |
| 2014/0046174 A1 | 2/2014 | Ladtkow et al. | |
| 2014/0276739 A1 | 9/2014 | Brannan et al. | |
| 2015/0148793 A1 | 5/2015 | Brannan | |
| 2015/0366612 A1* | 12/2015 | Crump | ............... A61B 18/1815 606/33 |

FOREIGN PATENT DOCUMENTS

| | | |
|---|---|---|
| CN | 108670174 A | 10/2018 |
| EP | 2522292 A1 | 11/2012 |

OTHER PUBLICATIONS

Examination Report issued in corresponding application EP 20709023.4 dated Feb. 8, 2024 (3 pages).
Extended European Search Report issued in corresponding application No. 25170760.0 dated Jul. 7, 2025.

* cited by examiner

INTERNALLY COOLED CERAMIC ELEMENT FOR A MICROWAVE ABLATION RADIATOR AND METHOD

CROSS-REFERENCE TO RELATED APPLICATIONS

This application is a U.S. National Stage Application filed under 35 U.S.C. § 371 (a) of International Patent Application No. PCT/US2020/016474, filed Feb. 4, 2020, which claims the benefit of the filing date of provisional U.S. Patent Application No. 62/801,691, filed Feb. 6, 2019.

FIELD

The present disclosure relates to a device and method for cooling a microwave ablation probe using a high dielectric ceramic element. The ceramic element, also referred to as a ceramic loading, includes lumens which enable a cooling fluid to flow in and out of the ceramic element, or includes a solid thermal conductor.

BACKGROUND

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat or ablate tissue.

Electrosurgical devices utilizing electromagnetic radiation have been developed for a variety of uses and applications. Typically, apparatus for use in ablation procedures include a power generation source, e.g., a microwave or radio frequency (RF) electrosurgical generator that functions as an energy source and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The particular type of tissue ablation procedure may dictate a particular ablation volume in order to achieve a desired surgical outcome. Ablation volume is correlated with antenna design, antenna performance, antenna impedance, ablation time and wattage, and tissue characteristics, e.g., tissue impedance.

Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to otherwise healthy tissue surrounding the tissue to which electrosurgical energy is being applied. Cooling a dielectrically-buffered microwave device used in ablation procedures would be useful.

SUMMARY

In an aspect of the present disclosure, a microwave antenna for ablating tissue in a patient is provided. The microwave antenna includes a radiator configured to radiate microwave radiation and a cable coupled to the radiator and including a fluid inflow line and a fluid outflow line. The ceramic element includes at least one internal channel configured to transport thermal energy away from the ceramic element.

In another aspect of the present disclosure, the at least one channel is in fluid communication with the fluid inflow line and/or the fluid outflow line.

In an aspect of the present disclosure, the at least one internal channel is at least two internal channels. In another aspect of the present disclosure, the at least one internal channel is two internal channels, and the two internal channels are in fluid communication at a distal end. One of the two internal channels is in fluid communication at a proximal end with the fluid inflow line, and the other of the two internal channels is in fluid communication at the proximal end with the fluid outflow line.

In yet another aspect of the present disclosure, the at least one internal channel is at least partially filled with at least one solid thermal conductor extending from the ceramic element to a chamber proximal the radiator. The chamber is in fluid communication with the fluid inflow line and the fluid outflow line. In an aspect of the present disclosure, the at least one solid thermal conductor is displaced from a central axis of the microwave antenna. In another aspect of the present disclosure, the at least one solid thermal conductor is at least two solid thermal conductors.

In yet another aspect of the present disclosure, the at least one solid thermal conductor is two solid thermal conductors and the two solid thermal conductors are positioned so that a central axis of the microwave antenna is disposed therebetween. The two solid thermal conductors are coupled by a helical formation in the chamber.

In an aspect of the present disclosure, the at least one solid thermal conductor is solid metal. In another aspect of the present disclosure, the at least one solid thermal conductor is electrically isolated from the microwave antenna.

A method for ablating tissue in a patient is provided. The method includes radiating, by a radiator, microwave radiation, and pumping fluid through a fluid inflow line of a cable. The method also includes disposing coaxially around the radiator a ceramic element. The ceramic element includes at least one internal channel configured to transport thermal energy away from the ceramic element.

A system for ablating tissue in a patient is provided. The system includes a radiator configured to radiate microwave radiation and a cable coupled to the radiator and including a fluid inflow line and a fluid outflow line. The system also includes a fluid supply system coupled to the cable and configured to provide a cooled fluid to the fluid inflow line, and a ceramic element coaxially disposed around the radiator. The ceramic element includes at least one internal channel configured to transport thermal energy away from the ceramic element.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

The present disclosure is generally directed to a microwave ablation antenna including a ceramic element, also referred to as a ceramic loading, surrounding the antenna. The ceramic loading has a high dielectric constant. However, as the ceramic element heats, the dielectric constant is reduced. Conventional ceramic loaded radiators do not cool the ceramic from within the ceramic, but rather terminate the cooling fluid proximal to the radiation section. The problem with this approach is the ceramic can significantly elevate in temperature during an ablation which causes the dielectric constant of the ceramic to drop. A drop in dielectric constant of the material surrounding the radiator causes wavelength elongation of energy on the radiator, destabilizing the energy pattern about the radiator.

In accordance with the present disclosure, a ceramic loading is cooled by fluid flowing through the ceramic itself, or by solid thermoconductive elements extending into the ceramic loading. Cooling the ceramic with fluid flowing within the ceramic reduces the dielectric constant drop by reducing temperature increase, thereby stabilizing the wavelength on the radiator and providing for a more predictable energy pattern.

According to an exemplary embodiment of the present disclosure, channels in the ceramic element are used to cool the ceramic element to maintain the high dielectric constant. The channels may be filled with a circulating fluid, which may be a liquid or a gas, and which may be pumped from an external source. The system may be closed and a cooling operation may be performed on the fluid after being pumped through the ceramic element and before being returned to cool the ceramic element again. Alternatively, the channels may be fully or partially filled with a solid thermoconductive element, which may be a metal. The thermoconductive element may extend proximally from the channels of the ceramic element into a fluid chamber which may be filled with a circulating fluid (liquid or gas) to cool the thermoconductive element. Utilizing cooled high dielectric ceramics to load microwave ablation probes stabilizes microwave energy patterns on radiators placed within tissue.

Hereinafter, embodiments of energy-delivery devices (also referred to as energy applicators), and systems including the same, of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "ablation procedure" generally refers to any ablation procedure, such as, for example, microwave ablation, radiofrequency (RF) ablation, or microwave or RF ablation-assisted resection. As it is used in this description, "energy applicator" generally refers to any device that can be used to transfer energy from a power generating source, such as a microwave or RF electrosurgical generator, to tissue. For the purposes herein, the term "energy applicator" is interchangeable with the term "energy-delivery device". As it is used in this description, "transmission line" generally refers to any transmission medium that can be used for the propagation of signals from one point to another. As it is used in this description, "fluid" generally refers to a liquid, a gas or both.

"Ceramic loading", "dielectric loading", or "ceramic element", refers to the material placed on the radiating elements of an ablation probe which should be cooled to stabilize the dielectric constant of the loading when heated during ablation. Ablation probes and/or antennas may be loaded with dielectric materials to impedance match the antenna impedance to the feedline impedance. Dielectric loading, also referred to as dielectric buffering, may also shape and stabilize the radiating pattern and radiator impedance from variations in local environment. A ray-dome may be used to determine and maintain radiator impedance and field pattern over varied environmental conditions. In this manner, a radiator may be balanced with dielectric loading. In still further alternatives, a dielectric lens may be used to shape the field pattern. The dielectric loading may be a single material type and one solid piece, or it may be layers or stacks of individual pieces with varying dielectric constants. Multiple pieces may provide design flexibility. For instance, the ceramic loading may include layers of dielectric, either nested cylinders (concentric) or stacked such that the material changes in the axial direction. Thin layers of heat shrink or vapor deposited coatings, for example Teflon, Paraleen, or similar, may be disposed over the ceramic to minimize sticking to tissue.

A function of the material loaded onto the radiator is to help determine and stabilize the electromagnetic field pattern generated by the radiator. The dielectric material is used to maximize energy transfer from the generator to the tissue by matching the impedance of the probe to the feedline. Heating of the ceramic loading element is not desirable. The tissue heating should primarily be caused by direct absorption of electromagnetic energy, and not thermal conduction from the probe.

The solid metal thermoconductors used to cool ceramic loading, as described herein, may be only passively coupled (also referred to as reactively coupled) to the primary, active radiating element of the microwave antenna.

The channels proposed herein may be straight or curved, and may be of constant diameter or variable diameter. The cross-sectional shape may be circular, square, or any other appropriate shape. The channels may form a helix, spiral or coil, which may have a constant or variable angle, and may include a second helix, spiral or coil. The spiral and helix shapes are applicable to both solid thermoconductors and fluid lumens. In the case of the fluid-filled channels, a second helix, spiral or coil may operate as a return channel. In the case of the solid thermal conductor, a second helix, spiral or coil may operate to balance the thermal sink.

In the fluid cooled lumen exemplary embodiment, pressure should be maintained to drive fluid into the small lumen through the ceramic. A diaphragm may be utilized to separate the inflow and outflow, and to hold some head pressure out to the ceramic. Perforations allowing some fluid communication between the inflow and outflow proximal to the ceramic loading may enable an adequate amount of fluid at lower temperature (i.e., not heated by ceramic cooling) to cool the device shaft.

The gas expansion chamber at the distal end operates based on Joule Thompson gas expansion. Compressed gas from inlet lumen would expand in this chamber causing a temperature drop. There may be more than one inlet lumen to this gas expansion chamber. One or more may end proximal to the ceramic, another within the ceramic. Flow through the channels and effective cooling through the ceramic calls for carrying a high pressure lumen out to the most distal portion of the flow path. The expansion chamber is co-located with the narrow inlet lumen(s) opening. A valve at the entrance to the gas expansion chamber may not be necessary, as the pressure drop may be primarily determined by the differential in cross sectional area of the flow channel. The small inlet lumen end at or within the larger gas expansion chamber determines the location of the pressure drop and consequent cooling.

Various embodiments of the present disclosure provide an energy-delivery device with a fluid filled antenna assembly. Embodiments may be suitable for utilization with hand-assisted, endoscopic and laparoscopic surgical procedures. Embodiments may be implemented using electromagnetic radiation at microwave frequencies, RF frequencies or at other frequencies. An electrosurgical system including the presently disclosed energy-delivery device with a fluid filled antenna assembly disposed in fluid communication with a fluid supply system via a hub 40 according to various embodiments is configured to operate at frequencies between about 300 MHz and about 10 GHz. During operation, the antenna assembly may enhance the overall heating pattern of the antenna assembly, prevent damage to the antenna assembly, and/or prevent harm to the clinician or patient.

Figure 1:
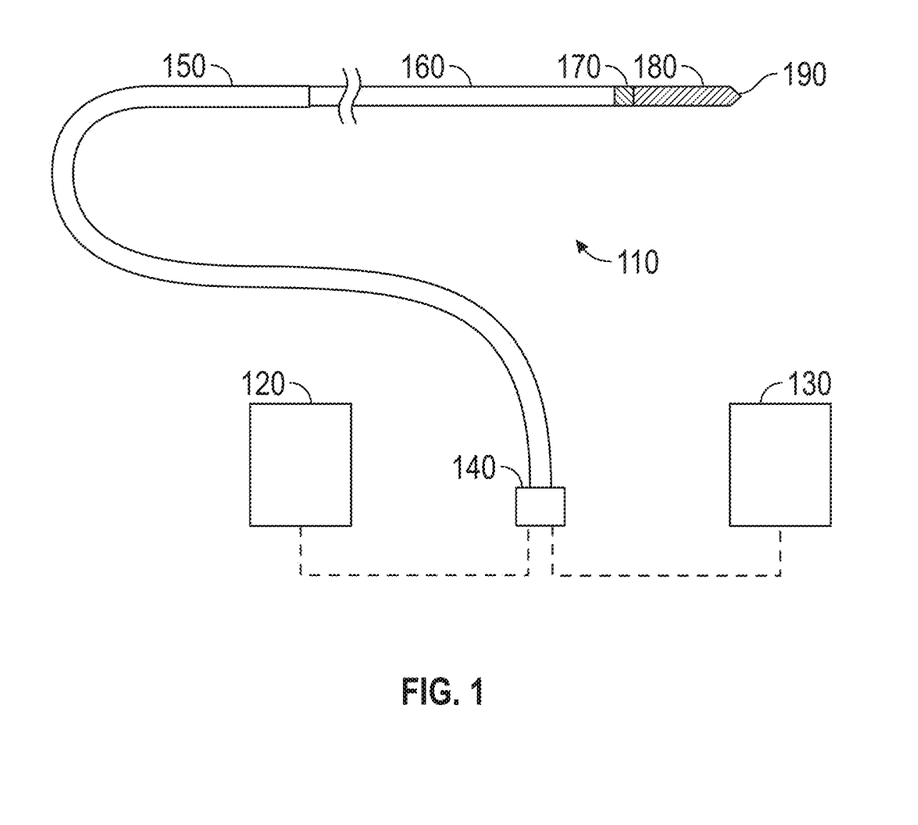
FIG. 1 is a schematic diagram of an energy applicator system including an energy applicator, an antenna, a fluid supply system, and a microwave power source in accordance with an embodiment of the present disclosure.

FIG. 1 is a schematic diagram of energy applicator system 100 including energy applicator 110, antenna 180, fluid supply system 120, and microwave power source 130 in accordance with an embodiment of the present disclosure. Antenna 180 may be a microwave antenna, and energy applicator 110 may be an ablation probe. Energy applicator system 100 includes feedline 150, probe 160, fluid chamber 170, and tip 190. Energy applicator system 100 also includes fluid supply system 120, microwave power source 130, and hub 140, which couples fluid supply system 120 and microwave power source 130 to feedline 150. Feedline 150 includes a cable for communicating microwave energy from microwave power source 130 to energy applicator 110, and also includes at least one fluid inflow channel and one fluid outflow channel. The fluid channels operate to bring cool fluid to energy applicator 110 and may be of any suitable shape, e.g., rectangular, cylindrical, etc.

Figure 2:
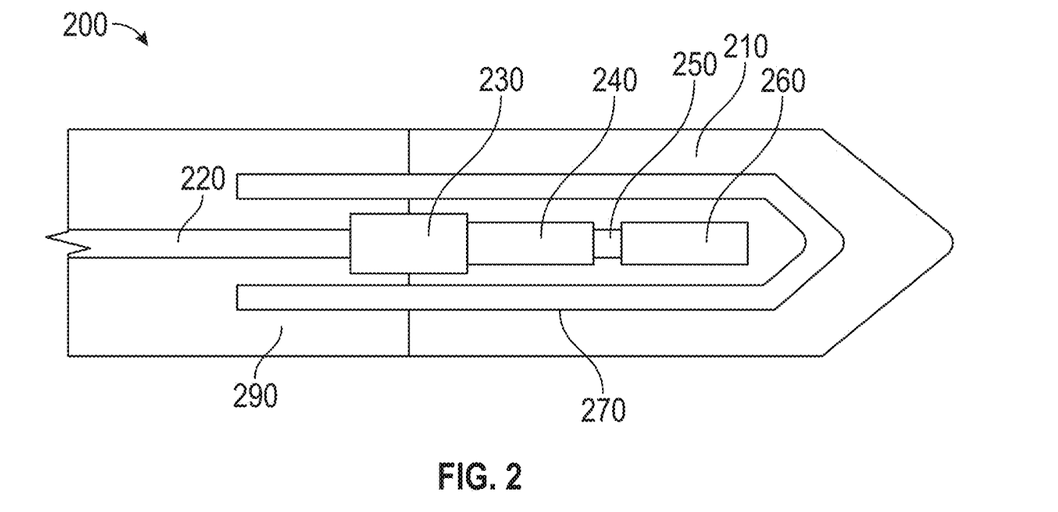
FIG. 2 is a longitudinal cross-sectional view of a distal portion of an antenna assembly in accordance with an embodiment of the present disclosure.

FIG. 2 is longitudinal cross-sectional view of a distal portion of antenna assembly 200 in accordance with an embodiment of the present disclosure. Antenna assembly 200 includes feedline 220 that couples to proximal radiating section 240 via balun (or choke) 230. Balun 230 may be composed of a material with high electromagnetic permeability such as, for example, iron, steel, ferrite, mu-metal, or any other suitable material, and may be Polytetrafluoroethylene (PTFE) with a coating of electromagnetic material. The electromagnetic material of balun 230 may be shorted to the outer conductor of the feedline. In alternative embodiments, balun 230 may not be used. Proximal radiating section 240 couples to distal radiating section 260 via feedgap 250. Ceramic load 210 (also referred to as ceramic element, ceramic loading, dielectric loading, and solid dielectric loading) surrounds and encases proximal radiating section 240, distal radiating section 260, and feedgap 250. Solid thermoconductor 270 occupies a lumen extending through ceramic load 210 and forming a U shape coupled at a distal end of antenna assembly 200. Solid thermoconductor 270 extends proximal to a proximal edge of ceramic load 210 into cooling chamber 290, which is supplied with cooling fluid to transport heat away from solid thermoconductor 270.

Figure 3:
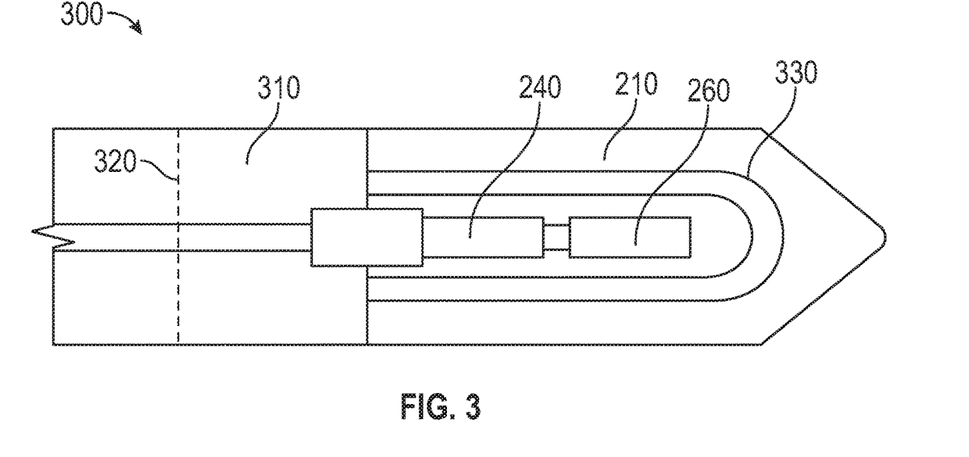
FIG. 3 is a longitudinal cross-sectional view of a distal portion of an antenna assembly in accordance with another embodiment of the present disclosure.
Figure 4:
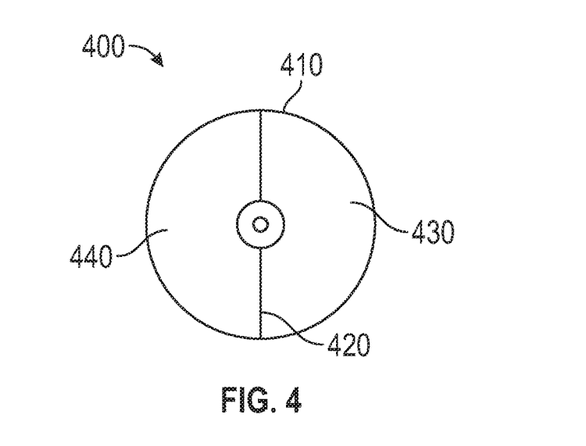
FIG. 4 illustrates a cross-sectional view along line 320 of FIG. 3 and shows a diaphragm in a fluid chamber in accordance with an embodiment of the present disclosure.

FIG. 3 is a longitudinal cross-sectional view of a distal portion of antenna assembly 300 in accordance with another embodiment of the present disclosure. Ceramic load 210 surrounds and encases proximal radiating section 240 and distal radiating section 260. Fluid flow channel 330 forms a U shape connected at a distal end of antenna assembly 300. One arm of fluid flow channel 330 is an inflow lumen, and the other arm is an outflow lumen. Alternative geometries for fluid flow channel 330, including multiple inflow and outflow lumens, are possible. Fluid flow channel 330 is in fluid communication with fluid chamber 310. Fluid chamber 310 is divided into sub-chambers, as shown in FIG. 4. One arm of fluid flow channel 330 is in fluid communication with one sub-chamber of fluid chamber 310, and the other arm of fluid flow channel 330 is in fluid communication with another sub-chamber of fluid chamber 310. Fluid chamber 310 also is in fluid communication with an external fluid cooling source, and in particular, one sub-chamber of fluid chamber 310 is in fluid communication with an inlet source of cooling fluid, and the sub-chamber of fluid chamber 310 is in fluid communication with a fluid outlet. Cross sectional line 320 crosses fluid chamber 310 which is proximal to a proximal edge of ceramic load 210.

FIG. 4 illustrates cross-section 400 cut along line 320 of FIG. 3. Cross-section 400 has outer circumference 410 and shows diaphragm 420 bisecting a fluid chamber into first sub-chamber 430 and second sub-chamber 440. One of the two sub-chambers is an inflow chamber, and the other is an outflow chamber. First sub-chamber 430, second sub-chamber 440, and diaphragm 420 maintain pressure to drive fluid into the small lumen through the ceramic load. Diaphragm 420 separates the inflow and outflow to hold head pressure out to a distal end of the ceramic. Perforations in diaphragm 420 allow some fluid to cross diaphragm 420 before the lumens through the ceramic loading to enable an adequate amount of fluid at lower temperature (i.e., not heated by ceramic cooling) to cool the device shaft.

Figure 5:
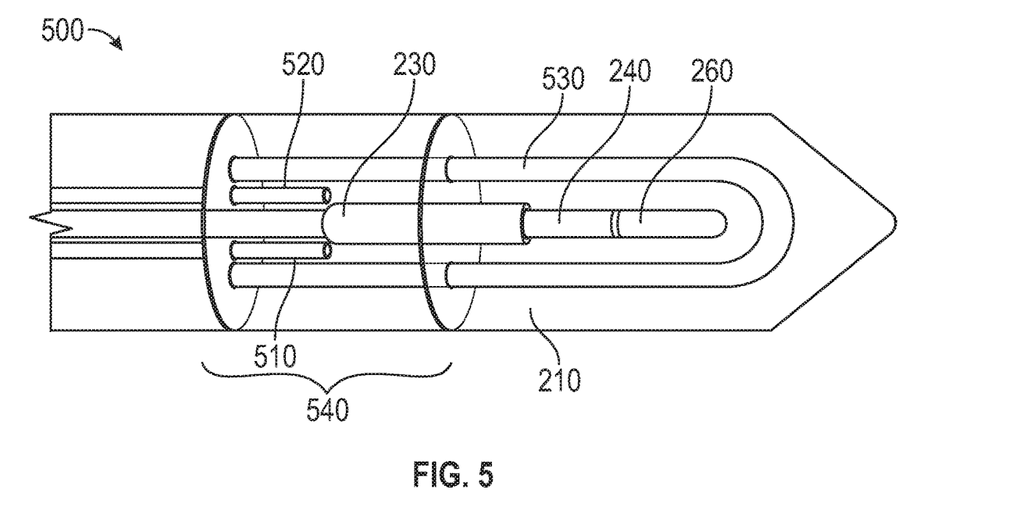
FIG. 5 is a longitudinal cross-sectional view of a distal portion of an antenna assembly in accordance with another embodiment of the present disclosure.

FIG. 5 is a longitudinal cross-sectional view of a distal portion of antenna assembly 500 in accordance with another embodiment of the present disclosure. Antenna assembly 500 includes cooling inflow line 510 and cooling outflow line 520, which are both in fluid communication with cooling chamber 540. Solid thermal conductor 530 extends into cooling chamber 540 to enable the transport of heat away from antenna assembly 500. Solid thermal conductor 530 also extends into ceramic load 210, and in this case forms a U shape. As discussed herein, alternative geometries for the lumen in ceramic load 210 occupied by solid thermal conductor 530 are also possible. Ceramic load 210 surrounds and encases distal radiating section 260, proximal radiating section 240, and optionally balun 230, which is itself optional.

Figure 6A:
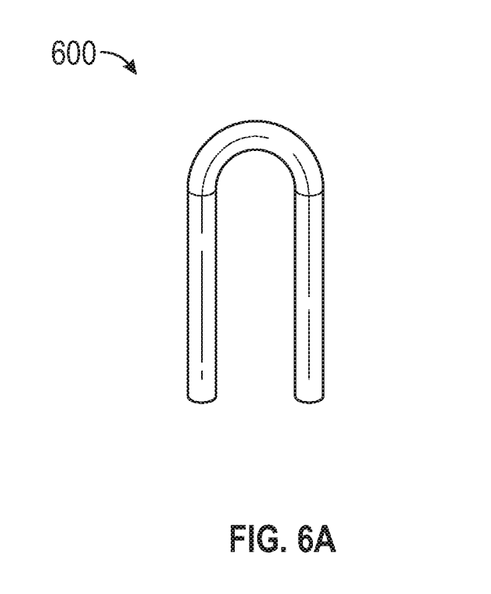
FIGS. 6A-6D illustrate different geometries for cooling lumens in accordance with embodiments of the present disclosure.
Figure 6B:
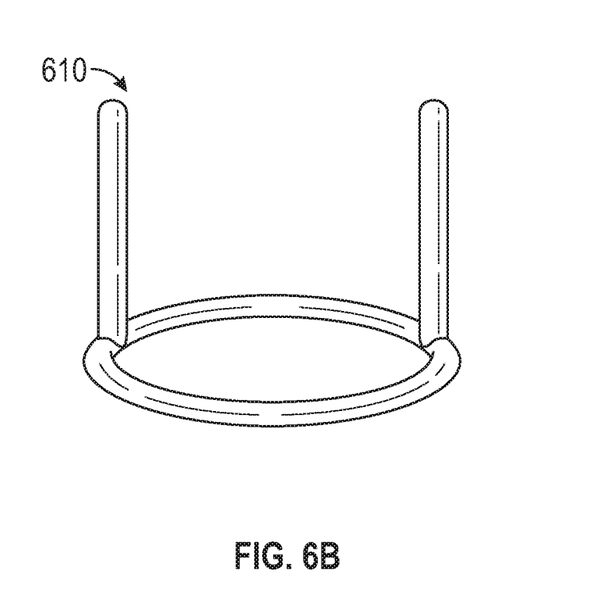
Figure 6C:
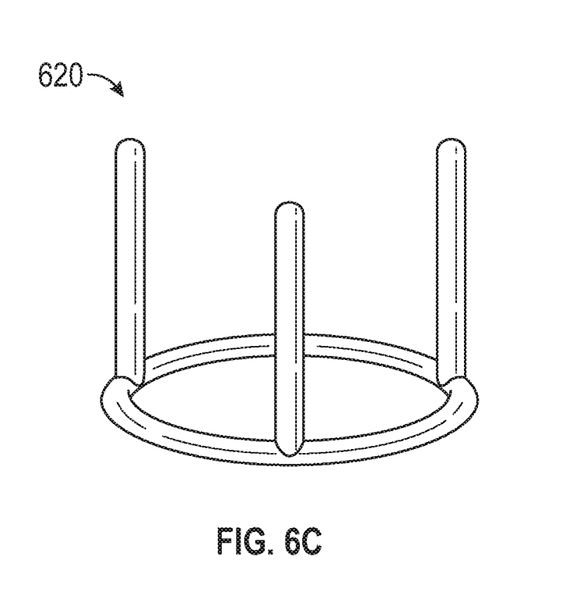
Figure 6D:
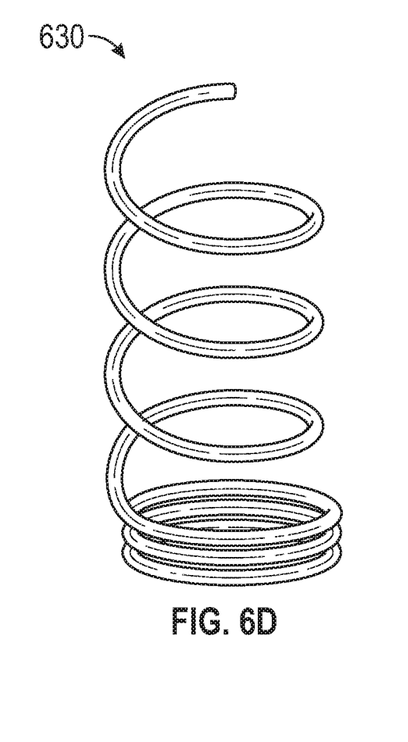

FIGS. 6A-6D illustrate different geometries for cooling lumens in accordance with embodiments of the present disclosure. The cooling lumens of FIGS. 6A-6D may be used to transport a cooling fluid (liquid or gas), or alternatively may be occupied by a solid thermoconductor. FIG. 6A illustrates lumen shape 600, which is also shown in FIGS. 2, 3, and 5. FIG. 6B illustrates lumen shape 610, FIG. 6C illustrates lumen shape 620, and FIG. 6D illustrates lumen shape 630, which is a helix. Lumen shape 630 may alternatively be a coil, a double helix. The helix or coil of lumen shape 630 may have variable diameter helix, variable size and shape of lumen cross-section, and/or constant or variable angle of the coil. The double helix variation of lumen shape 630 may by coupled at the distal end to allow one strand of the double helix to allow inflow of a cooling fluid and the other strand of the double helix to allow outflow of the cooling fluid.

Figure 7:
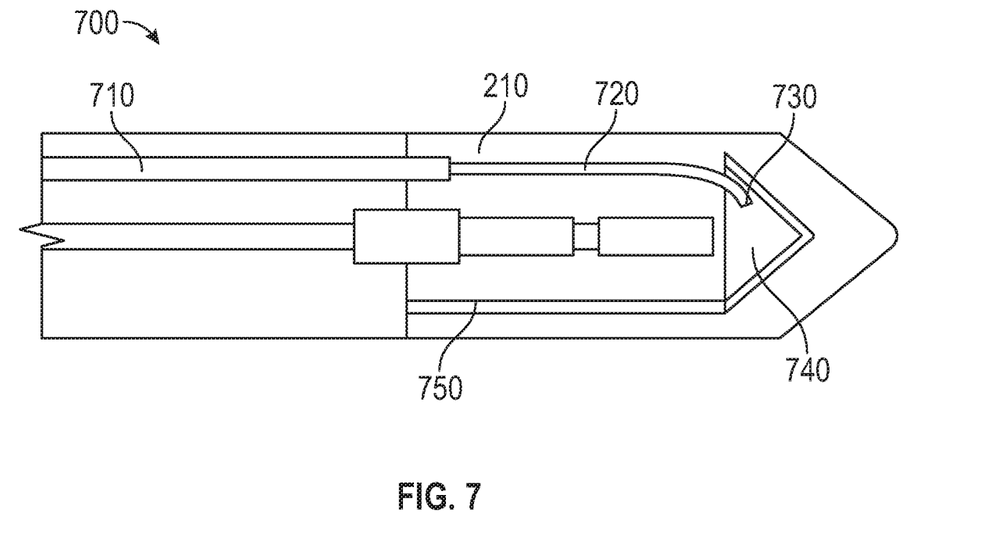
FIG. 7 is a longitudinal cross-sectional view of a distal portion of another antenna assembly in accordance with an embodiment of the present disclosure.

FIG. 7 is a longitudinal cross-sectional view of a distal portion of antenna assembly 700 in accordance with an embodiment of the present disclosure. Antenna assembly 700 uses compressed gas as a cooling fluid, which is supplied by inflow tube 710. Gas inflow tube 710, which may be metal, supplies the compressed gas to inlet lumen 720. Inlet lumen 720, which may also be referred to as a delivery lumen, extends through ceramic load 210 and terminates at inlet lumen opening 730. Inlet lumen opening 730 opens into gas expansion chamber 740. The compressed gas from inlet lumen 720 would expand after passing through inlet lumen opening 730 into gas expansion chamber 740, thereby realizing a temperature drop due to Joule Thompson gas expansion. Inlet lumen opening 730 is a narrow inlet co-located with gas expansion chamber 740, and consequently a valve is not necessary to achieve a pressure drop, which may be primarily determined by the differential in cross sectional space of the flow path. Outlet lumen 750, also referred to as a return lumen, would also have an opening in gas expansion chamber 740 to enable the expanded gas to return to a fluid chamber proximal to the ceramic loading, or optionally, directly to a return line flowing back to the fluid cooling system.

Alternative exemplary embodiments may include more than one inlet or outlet to gas expansion chamber 740, and/or a different positioning or multiple gas expansion chambers. In still further alternative exemplary embodiments, multiple inflow tubes 710 may be provided and one or more of these inflow tubes 710 may end proximal to the ceramic, while others end within ceramic load 210.

Figure 8:
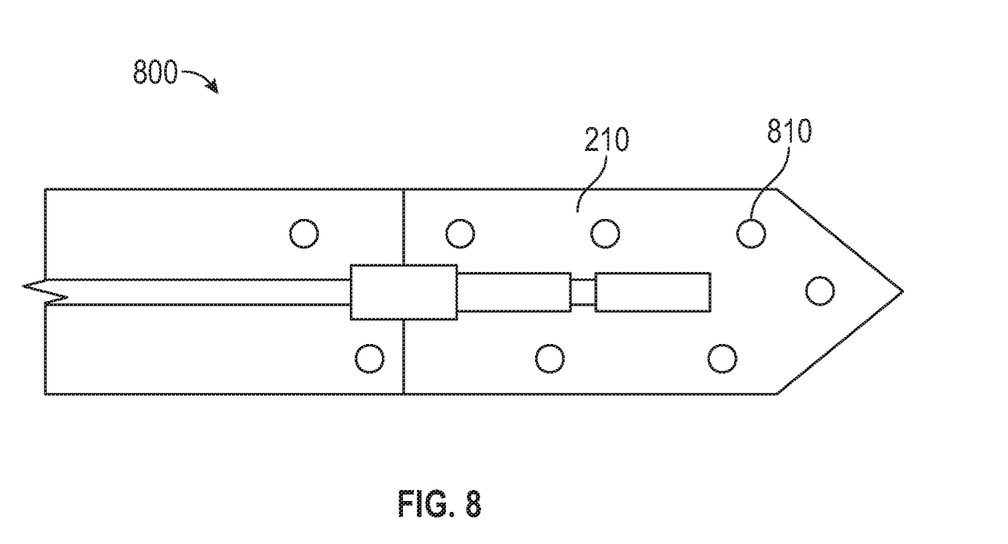
FIG. 8 is a longitudinal cross-sectional view of a distal portion of another antenna assembly in accordance with an embodiment of the present disclosure.

FIG. 8 is a longitudinal cross-sectional view of a distal portion of antenna assembly 800 in accordance with an embodiment of the present disclosure. Antenna assembly 800 includes lumen cross section pattern 810, which may be a spiral or coil shape, and which may be occupied by a solid thermoconductor or may represent a flow path for a cooling fluid. One end of the flow path connects to an inlet channel and the other end connects to an outlet channel. In FIG. 8, the lumen represented by lumen cross section pattern 810 is a single spiral and/or coil.

Figure 9:
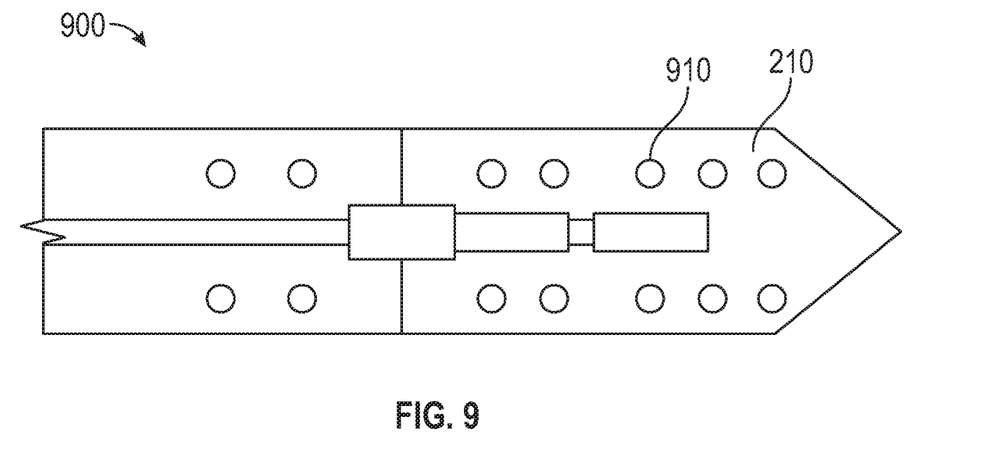
FIG. 9 is a longitudinal cross-sectional view of a distal portion of another antenna assembly in accordance with an embodiment of the present disclosure.

FIG. 9 is a longitudinal cross-sectional view of a distal portion of antenna assembly 900 in accordance with an embodiment of the present disclosure. Antenna assembly 900 includes lumen cross section pattern 910, which may be a spiral or coil shape, and which may be occupied by a solid thermoconductor or may represent a flow path for a cooling fluid. One end of the flow path connects to an inlet channel and the other end connects to an outlet channel. In contrast to FIG. 8, the lumen in FIG. 9 represented by lumen cross section pattern 910 are two nested spiral/coils, which may or may not be connected at the distal end.

Figure 10:
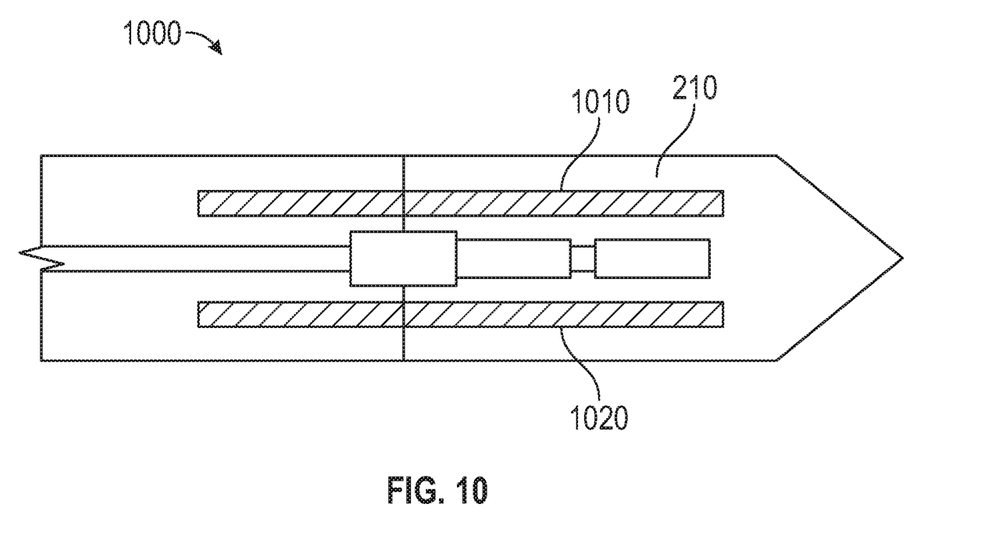
FIG. 10 is a longitudinal cross-sectional view of a distal portion of another antenna assembly in accordance with an embodiment of the present disclosure.

FIG. 10 is a longitudinal cross-sectional view of a distal portion of antenna assembly 1000 in accordance with an embodiment of the present disclosure. Antenna assembly 1000 includes lumen cross section pattern 810, which may include first solid rod thermoconductor 1010 and second solid rod thermoconductor 1020.

The cooling fluid may be any suitable fluid that can be used for cooling the antenna assembly, e.g., deionized water. The cooling fluid composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the fluid.

Examples of fluid supply system embodiments are disclosed in commonly assigned U.S. patent application Ser. No. 12/566,299 filed on Sep. 24, 2009, entitled "OPTICAL DETECTION OF INTERRUPTED FLUID FLOW TO ABLATION ANTENNA", and U.S. application Ser. No. 13/835,625 filed on Mar. 15, 2013 entitled "RECIRCULATING COOLING SYSTEM FOR ENERGY DELIVERY DEVICE" the disclosure of which is incorporated herein by reference.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave antenna for ablating tissue in a patient, comprising:
   a radiator configured to radiate microwave radiation;
   a cable coupled to the radiator and including a fluid inflow line and a fluid outflow line; and
   a ceramic element forming a distal-most tip of the microwave antenna and coaxially disposed around the radiator, the ceramic element including at least one internal channel configured to transport thermal energy away from the ceramic element, wherein the at least one internal channel is at least partially filled with at least one solid thermal conductor disposed distal to a distal-most end of the radiator.

2. The microwave antenna according to claim 1, wherein the at least one internal channel is in fluid communication with at least one of the fluid inflow line and the fluid outflow line.

3. The microwave antenna according to claim 1, wherein the at least one internal channel is at least two internal channels.

4. The microwave antenna according to claim 1, wherein the at least one internal channel is two internal channels, the two internal channels being in fluid communication at a distal end, one of the two internal channels being in fluid communication at a proximal end with the fluid inflow line, the other of the two internal channels being in fluid communication at the proximal end with the fluid outflow line.

5. The microwave antenna according to claim 1, wherein the at least one solid thermal conductor extends from the ceramic element to a chamber proximal to the radiator, the chamber being in fluid communication with the fluid inflow line and the fluid outflow line.

6. The microwave antenna according to claim 1, wherein the at least one solid thermal conductor is displaced from a central axis of the microwave antenna.

7. The microwave antenna according to claim 1, wherein the at least one solid thermal conductor is at least two solid thermal conductors.

8. The microwave antenna according to claim 5, wherein:
   the at least one solid thermal conductor are two solid thermal conductors;
   the two solid thermal conductors are positioned so that a central axis of the microwave antenna is disposed therebetween; and
   the two solid thermal conductors are coupled by a helical formation in the chamber.

9. The microwave antenna according to claim 1, wherein the at least one solid thermal conductor is solid metal.

10. A method for ablating tissue in a patient, comprising:
    radiating, by a radiator of a microwave antenna, microwave radiation;
    pumping fluid through a fluid inflow line of a cable; and
    disposing coaxially around the radiator a ceramic element, the ceramic element forming a distal-most tip of the microwave antenna and including at least one internal channel configured to transport thermal energy away from the ceramic element, wherein the at least one internal channel is at least partially filled with at least one solid thermal conductor disposed distal to a distal-most end of the radiator.

11. The method according to claim 10, wherein the at least one internal channel is in fluid communication with at least one of the fluid inflow line and a fluid outflow line of the cable.

12. The method according to claim 10, wherein the at least one internal channel is at least two internal channels.

13. The method according to claim 10, wherein the at least one internal channel is two internal channels, the two internal channels being in fluid communication at a distal end, one of the two internal channels being in fluid communication at a proximal end with the fluid inflow line, the other of the two internal channels being in fluid communication at the proximal end with the fluid outflow line.

14. The method according to claim 10, wherein the at least one solid thermal conductor extends from the ceramic element to a chamber in fluid communication with at least one of the fluid inflow and fluid outflow lines.

15. The method according to claim 10, wherein the at least one solid thermal conductor is displaced from a central axis of the microwave antenna.

16. The method according to claim 10, wherein the at least one solid thermal conductor is at least two solid thermal conductors.

17. The method according to claim 16, wherein:
    the at least one solid thermal conductor are two solid thermal conductors;
    the two solid thermal conductors are positioned so that a central axis of the microwave antenna is disposed therebetween; and
    the two solid thermal conductors are coupled by a helical formation in the chamber.

18. A system for ablating tissue in a patient, comprising:
    a microwave antenna including a radiator configured to radiate microwave radiation;
    a cable coupled to the radiator and including a fluid inflow line and a fluid outflow line;
    a fluid supply system coupled to the cable and configured to provide a cooled fluid to the fluid inflow line; and
    a ceramic element forming a distal-most tip of the microwave antenna and coaxially disposed around the radiator, the ceramic element including at least one internal channel configured to transport thermal energy away from the ceramic element, wherein the at least one internal channel is at least partially filled with at least one solid thermal conductor disposed distal to a distal-most end of the radiator.

* * * * *